United States Patent [19]

Torisu et al.

[11] 3,959,318

[45] May 25, 1976

[54] PROCESS FOR PREPARING HIGHLY PURE 5-NITRO-1,4,4A,9A-TETRAHYDROAN-THRAQUINONE

[75] Inventors: Yasuyoshi Torisu, Yanagawa; Seishichiro Kaba, Arao; Ken Mukai, Omuta, all of Japan

[73] Assignee: Mitsui Toatsu Chemicals, Incorporated, Tokyo, Japan

[22] Filed: Sept. 5, 1975

[21] Appl. No.: 610,778

[30] Foreign Application Priority Data

Sept. 6, 1974 Japan............................ 49-101914

[52] U.S. Cl. ............................................. 260/369
[51] Int. Cl.² ........................................ C07C 49/68
[58] Field of Search .................................. 260/369

[56] References Cited
UNITED STATES PATENTS

| | | |
|---|---|---|
| 2,495,222 | 1/1950 | Dawsey et al....................... 260/369 |
| 3,838,178 | 9/1974 | Vaughan............................. 260/369 |
| 3,888,890 | 6/1975 | Kirchner et al..................... 260/369 |

*Primary Examiner*—Paul F. Shaver
*Attorney, Agent, or Firm*—Fisher, Christen & Sabol

[57] ABSTRACT

Highly pure 5-nitro-1,4,4a,9a-tetrahydroanthraquinone can be obtained by subjecting 6-nitronaphthoquinone-containing crude 5-nitro-1,4-naphthoquinone to Diels-Alder condensation reaction with 1,3-butadiene in a solvent including benzene, an alkylated aromatic hydrocarbon such as toluene, xylene or the like, a halogenated aromatic hydrocarbon such as chlorobenzene, dichlorobenzene, or the like, or a halogenated aliphathic hydrocarbon such as trichloroethylene, perchloroethylene or the like, cooling the resulting reaction solution to crystallize the reaction product, and separating the thus crystallized product by filtration. 5-nitro-1,4,4a,9a-tetrahydroanthraquinone has a relatively small solubility in the above-mentioned solvents, while the solubility of 6-nitro-1,4.4a,9a-tetrahydroanthraquinone in the solvents is rather great, thus the above-mentioned solvents being effective for the separation of these compounds from each other. The oxidation and the subsequent reduction of the thus obtained 5-nitro-1,4,4a,9a-tetrahydroanthraquinone yields 1-aminoanthraquinone with a purity above 98 wt% and a 2-aminoanthraquinone content below 1 wt%. The above-mentioned solvents are also effective for purification of 6-nitro-1,4,4a,9a-tetrahydroanthraquinone-containing 5-nitro-1,4,4a,9a-tetrahydroanthraquinone by recrystallization.

13 Claims, No Drawings

PROCESS FOR PREPARING HIGHLY PURE 5-NITRO-1,4,4A,9A-TETRAHYDROANTHRAQUINONE

BACKGROUND OF THE INVENTION

1. Field of the Invention

This invention relates to a process for preparing 5-nitro-1,4,4a,9a-tetrahydroanthraquinone (hereinafter referred to simply as 5-nitrotetrahydroanthraquinone). 1-aminoanthraquinone which is important as a dye intermediate can be readily obtained by oxidizing 5-nitrotetrahydroanthraquinone to form 1-nitroanthraquinone and reducing the 1-nitroanthraquinone.

2. Description of the Prior Art

In the production of 1-aminoanthraquinone, it is the common practice to aminate anthraquinone-1-sulfonic acid which is obtained by sulfonation of anthraquinone. However, this amination process involves some environmental problems such as a bad working environment and a waste liquor treatment since mercury is essentially required as a catalyst for sulfonation.

Under these circumstances, there have been proposed many processes for the preparation of 1-aminoanthraquinone, including, for example, a process (West Germany, OLS 2162538) wherein 1-aminoanthraquinone is formed through 1-nitroanthraquinone obtained by nitration of anthraquinone with concentrated nitric acid, and a process (West Germany, OLS 2103360) wherein anthraquinone is nitrated with nitric acid in phosphoric acid to obtain 1-nitroanthraquinone, followed by reduction to yield 1-aminoanthraquinone. However, these processes are disadvantageous from an industrial point of view in that a large quantity of the waste acid must be treated in a suitable manner and that the processes involve formation of by-products such as dinitroanthraquinone, 2-nitroanthraquinone and the like, so that a purifying step or system which requires a great deal of labor and cost is essential for obtaining highly pure 1-aminoanthraquinone.

While, there have been proposed several other processes wherein 5-nitroanaphthoquinone is condensed with 1,3-butadiene to form 5-nitrotetrahydroanthraquinone, followed by oxidation to obtain 1-nitroanthraquinone. In this instance, according to N.N.Woroshtzov (Khim, Nauka i Prom., 5, 474-475 (1960), 5-nitronaphthoquinone is subjected to react with 1,3-butadiene in methanol to result 5-nitrotetrahydroanthraquinone, which is then isolated and oxidized by air in an alcoholic alkali solution to obtain 1-nitroanthraquinone. Further, the French Pat. No. 1,486,803 describes the production of 1-nitroanthraquinone by reacting 5-nitroanthraquinone with 1,3-butadiene in nitrobenzene and subjecting the resultant reaction solution to oxidation in the presence or absence of piperidine to obtain 1-nitroanthraquinone. 1-nitroanthraquinone obtained by these processes can be readily reduced into 1-aminoanthraquinone by an ordinary method.

In general, 1-aminoanthraquinone which is to be employed as an intermediate for dye is preferred to have a purity of greater than about 98 wt% and a 2-aminoanthraquinone content as low as 1 wt%. The above-mentioned prior processes have, respectively, the following problems for economically supplying 1-aminoanthraquinone with such high purity.

5-nitronaphthoquinone which is used as a starting material in these processes is generally prepared from 1,4-naphthoquinone by nitration. In the nitration, an isomer, 6-nitronaphthoquinone, is also secondarily produced, so that crude 5-nitronaphthoquinone obtained after the nitration generally contains 5 to 20 wt% of 6-nitroanaphthoquinone.

According to the supplemental test conducted by us, when 6-nitronaphthoquinone-containing 5-nitronaphthoquinone (hereinafter referred to simply as crude 5-nitronaphthoquinone) used as a starting material is subjected to condensation with 1,3-butadiene and to oxidation and reduction in accordance with the process of Woroshtzov using ethanol as a solvent, 6-nitronaphthoquinone is successively converted into 6-nitro-1,4,4a,9a-tetrahydroanthraquinone (hereinafter referred to as 6-nitrotetrahydroanthraquinone), 2-nitroanthraquinone, and 2-aminoanthraquinone, which contaminate corresponding 5-nitrotetrahydroanthraquinone, 1-nitroanthraquinoone, and 1-aminoanthraquinone, respectively, thus it being difficult to obtain highly pure 1-nitrotetrahydroanthraquinone, 1-nitroanthraquinone or 1-aminoanthraquinone. In order to obtain these compounds with high purity, it is undesirably necessitated to purify the starting material, the intermediate or the final product, in additional purifying steps.

In the process of the French Pat. No. 1,486,803, 5-nitrotetrahydroanthraquinone produced is directly subjected to oxidation, without isolation from reaction system, into 1-nitroanthraquinone. Accordingly, when crude 5-nitronaphthoquinone is used as a starting material, 6-nitroanaphthoquinone is converted into 2-nitronaphthoquinone through 6-nitrotetrahydroanthraquinone, thus contaminating 1-nitroanthraquinone and lowering the purity thereof. Further, it is difficult to obtain highly pure 1-aminoanthraquinone from the thus contaminated 1-nitroanthraquinone. This process also requires an additional step of purifying the starting material or the product so as to obtain highly pure 1-nitroanthraquinone or 1-aminoanthraquinone. In this connection, we have found as a result of an experiment that when crude 5-nitronaphthoquinone is condensed with 1,3-butadiene in nitrobenzene and the resulting product is separated or isolated from the reaction system by filtration, most of 6-nitrotetrahydroanthraquinone produced from 6-nitronaphthoquinone is removed in a state of being dissolved in the solvent, so that there can be obtained highly pure 5-nitrotetrahydroanthraquinone, from which 1-nitroanthraquinone or 1-aminoanthraquinone with high purity can be prepared. However, this process is also industrially disadvantageous in that the dissolution loss of 5-nitrotetrahydroanthraquinone in solvent is large, it's yield being considerably reduced.

In order to produce highly pure 1-aminoanthraquinone in an economical manner, it is desirable to prepare 1-aminoanthraquinone with high purity from crude 5-nitronaphthoquinone without purification of the starting material, an intermediate and an ultimate product. This is very hard to achieve by the above-mentioned prior processes.

SUMMARY OF THE INVENTION

It is therefore an object of the present invention to provide a process for the preparation of 5-nitrotetrahydroanthraquinone with high purity.

It is another object of the present invention to provide a process for the preparation of highly pure 5-nitrotetrahydroanthraquinone directly from crude 5- nitronaphthoquinone.

These and other objects can be achieved by (A) reacting 5-nitronaphthoquinone with 1,3-butadiene in a solvent selected from the group consisting of benzene, an alkylated aromatic hydrocarbon, a halogenated aromatic hydrocarbon, a halogenated aliphatic hydrocarbon, and a mixture thereof, cooling the resulting reaction solution to crystallize the reaction product, and separating the thus crystallized product from the reaction system by filtration; or (B) reacting crude 5-nitronaphthoquinone with 1,3-butadiene to obtain 6-nitrotetrahydroanthraquinone-containing 5-nitrotetrahydroanthraquinone (hereinafter referred to as crude 5-nitrotetrahydroanthraquinone), dissolving the crude 5-nitrotetrahydroanthraquinone in the above-indicated solvent under heating conditions, subjecting the resulting solution to filtration, cooling the filtrate to crystallize 5-nitrotetrahydroanthraquinone, and separating the thus crystallized product by filtration.

The crude 5-nitronaphthoquinone useful in the present invention may contain 6-nitronaphthoquinone in an amount of less than 20 wt% on a dry basis and may be in the form of a wet cake with a water content below 50 wt%. While, the crude 5-nitrotetrahydroanthraquinone intends to mean one which contains 6-nitrotetrahydroanthraquinone in an amount below 10wt%.

We have made an intensive study on solubilities of 5-nitrotetrahydroanthraquinone and 6-nitrotetrahydroanthraquinone in various kinds of solvents and found that 5-nitrotetrahydroanthraquinone has a relatively small solubility in a solvent such as benzene, an alkylated or halogenated aromatic hydrocarbon or a halogenated aliphatic hydrocarbon and that the solubility ratios of 6-nitrotetrahydroanthraquinone to 5-nitrotetrahydroanthraquinone in the solvents above are extremely high compared with those in other solvents such as alcohols and ketones. The use of these solvents in the condensation of crude nitronaphthoquinone and 1,3-butadiene or in the purification of the resulting condensate results in high yield of highly pure 5-nitrotetrahydroanthraquinone.

That is, highly pure 5-nitrotetrahydroanthraquinone can be obtained at high yield by condensing crude 5-nitronaphthoquinone with 1,3-butadiene in benzene, an alkylated or halogenated aromatic hydrocarbon, or a halogenated aliphatic hydrocarbon, followed by cooling and filtration. The above-mentioned solvent is also useful for purifying 5-nitrotetrahydroanthraquinone which contains a substantial amount of 6-nitrotetrahydroanthraquinone.

Thus, it is made possible to economically produce highly pure 1-aminoanthraquinone from crude 5-nitronaphthoquinone Only for reference, there are shown in Table 1 the solubilities of 5-nitrotetrahydroanthraquinone and 6-nitrotetrahydroanthraquinone in various kinds of solvents. From the Table it will be understood that benzene, the alkylated or halogenated aromatic hydrocarbon, or the halogenated aliphatic hydrocarbon is excellent as a condensation solvent for crude 5-nitronaphthoquinone or as a solvent for purifying 5-nitrotetrahydroanthraquinone which contains a substantial amount of 6nitrotetrahydroanthraquinone. The ethanol solvent used by Woroshtzov is low in solubility ratio of 6-nitrotetrahydroanthraquinone to 5-nitrotetrahydroanthraquinone, so that it is difficult to obtain 5-nitrotetrahydroanthraquinone with high purity when 5-nitrotetrahydroanthraquinone is isolated after the condensation. While, though the nitrobenzene solvent has a relatively high solubility ratio of 6-nitrotetrahydroanthraquinone to 5-nitrotetrahydroanthraquinone, the solubility of 5-nitrotetrahydroanthraquinone in nitrobenzene is extremely high, lowering the yield thereof. This coincides with the results of the supplemental test conducted by us.

Table 1

| Solvent | Solubility of 5- or 6- Nitrotetrahydroanthraquinone (at 25°C) | | 6-nitro**/5-nitro* solubility ratio |
|---|---|---|---|
| | Solubility | | |
| | 5-nitro* | 6-nitro** | |
| ethanol | less than 0.1 | less than 0.05 | 0.50 |
| methoxyethanol | 1.8 | 0.8 | 0.44 |
| methyl ethyl ketone | 6.9 | 6.9 | 1.00 |
| nitrobenzene | 9.3 | 10.7 | 1.15 |
| benzene | 4.2 | 5.8 | 1.38 |
| toluene | 3.1 | 4.9 | 1.58 |
| o-dichlorobenzene | 2.4 | 5.2 | 2.17 |
| trichloroethylene | 0.9 | 3.7 | 4.11 |

Note:
The solubility is expressed in terms of parts by weight of 5- or -6 nitrotetrahydroanthraquinone dissolved in 100 parts by weight of solvent.
*The term "5-nitro" herein used intends to mean 5-nitrotetrahydroanthraquinone.
**The term "6-nitro" intends to mean 6-nitrotetrahydroanthraquinone.

DETAILED DESCRIPTION OF PREFERRED EMBODIMENTS

In one embodiment (A) of the present invention, crude 5-nitronaphthoquinone and 1,3-butadiene are subjected to condensation reaction in benzene, an alkylated aromatic hydrocarbon, a halogenated aromatic hydrocarbon or a halogenated aliphatic hydrocarbon, the resulting reaction solution is cooled to crystallize the reaction product, and the thus crystallized product is separated from the solution by filtration. The crude 5-nitronaphthoquinone used as a starting material is generally obtained by nitration of 1,4-naphthoquinone by means of nitric acid or a mixed acid of nitric acid and sulfuric acid, and may contain 6-nitronaphthoquinone and other byproducts (tarry matter) formed upon the nitration. The crude 5-nitronaphthoquinone may be subjected to the condensation reaction in the form of a wet cake which contains water up to about 50 wt%. Though the content of 6-nitronaphthoquinone is preferred to be as low as possible, the crude 5-nitronaphthoquinone which contains 6-nitronaphthoquinone up to 20 wt% is usable in practical application.

Examples of the solvents are benzene, alkylated aromatic hydrocarbons having one to three substituted alkyl groups each containing 1 to 4 carbon atoms and including toluene, xylene, methylnaphthalene and the like, halogenated aromatic hydrocarbons having one to three substituted halogen atoms and including chlorobenzene, dichlorobenzene, trichlorobenzene, bromobenzene, chloronaphthalene and the like, and halogenated aliphatic hydrocarbons having from 1 to 4 carbon atoms and one to four substituted halogen atoms and including chloroform, tetrachloromethane, fluorotrichloromethane, dichloroethane, trichloroethane, tetrachloroethane, dibromoethane, dichloropropane, trichloroethylene, perchloroethylene and the like. These solvents may be used singly or in combination. Upon consideration of toxity, easiness of recovery, and cost, benzene, toluene, xylene, dichlorobenzene, trichloroethylene, and perchloroethylene are most suitable for the purpose of the present invention from an industrial viewpoint. The amount of solvent is generally 1 to 15 times as much as that of crude 5-nitronaphthoquinone on a weight basis. Especially when there is used crude 5-naphthoquinone which contains 5 to 15 wt% of 6-nitronaphthoquinone, the amount is preferred to be 2 to 5 times as much. Though the solvent may be employed in an amount of greater than 15 times by weight as much as that of crude 5-nitronaphthoquinone, the yield of the reaction product, 5-nitrotetrahydroanthraquinone, will be undesirably lowered. It should be noted that even though the amount of the solvent used in the present invention is reduced, the purity of the reaction product is hardly lowered.

The amount of 1,3-butadiene used is generally in the range of 1.0 to 3.0, preferably 1.5 to 2.5 mols per mol of 5-nitronaphthoquinone.

The reaction is generally effected in an autoclave at a temperature of 50° to 100°C, preferably 70° to 90°C. The reaction pressure is in the range of 1 to 4 kg/cm$^2$G, preferably 2 to 3 kg/cm$^2$G. In case where the amount of solvent is relatively small with respect to crude 5-nitronaphthoquinone though it is within the above-defined range, a part of the crude 5-nitronaphthoquinone is not necessarily dissolved at an initial stage of reaction and may be suspended in the solvent. However, this does not disturb the progress of the reaction: crude 5-nitronaphthoquinone is gradually dissolved as the reaction proceeds thereby to form a uniform solution. The reaction should be continued until the starting 5-nitronaphthoquinone is completely consumed. The time required for the complete consumption is roughly in the range of about 1 to 10 hours, and 2 to 6 hours under normal conditions.

Upon cooling the thus obtained uniform reaction solution to below 40°C, preferably 20° to 30°C, 5-nitrotetrahydroanthraquinone crystarize out of solution. Then, the 5-nitrotetrahydroanthraquinone is separated from the reaction solution by filtration, washed with a solvent, and dried, if necessary. The solvent for washing is preferred to be miscible with the reaction solvent and water and to have small solubility for 5-nitrotetrahydroanthraquinone, and includes, for example, methanol, ethanol or propanol. The amount of the washing solvent is in the range of 1.5 to 5 times by weight as much as that of 5-nitrotetrahydroanthraquinone. The drying is generally effected under a normal or reduced pressure and the drying temperature is preferable to be below 100°C.

The excesses of 1,3-butadiene and the solvent may be recovered and reused.

Upon consideration of analytical accuracy, the quality of the thus obtained highly pure 5-nitrotetrahydroanthraquinone should be determined by oxiding it into 1-nitroanthraquinone and reducing the 1-nitroanthraquinone into 1-aminoanthraquinone by a standard method as will be described hereinlater, and then subjecting the 1-aminoanthraquinone to determination of a purity of 1-aminoanthraquinone, a content of 2-aminoanthraquinone and a content of other impurities. By the present invention, 1-aminoanthraquinone which is obtained by oxidation of the highly pure 5-nitrotetrahydroanthraquinone and then by reduction of the resulting 1-nitroanthraquinone by standard method has generally a purity of greater than 98 wt% and a 2-aminoanthraquinone content of less than 1 wt%, other impurities being scarecely detected.

The standard method wherein 5-nitrotetrahydroanthraquinone is oxidized into 1-nitroanthraquinone and then reduced into 1-aminoanthraquinone is illustrated in the following.

100 parts by weight of 5-nitrotetrahydroanthraquinone is added to and suspended in 1500 parts by weight of ethanol, to which is added 38.5 parts by weight of a 40 wt% sodium hydroxide aqueous solution, followed by agitation at about 75°C for 3 hours. Then, the resultant solution is cooled down to about 10°C, followed by filtration, washing with water and dripping. The resulting wet cake is then introduced into 1500 parts by weight of water for suspension, into which is dropped 990 parts by weight of a 16 wt% sodium sulfide aqueous solution at 95°C over a period of about 30 min with agitation, followed by further agitation at 95°C for 1 hour. The resultant solution is subjected to filtration followed by cooling to crystalize 1-aminoanthraquinone, then the 1-aminoanthraquinone is separated by filtration, washed with water and dried at 85°–95°C. The purity of 1-aminoanthraquinone thus obtained is determined by a KBr method using an infrared absorption spectrum.

One of features of the above-mentioned process of the invention is that highly pure 5-nitrotetrahydroanthraquinone can be obtained at high yield by using as a starting material crude 5-nitronaphthoquinone without purification which contains a relatively large amount of 6-nitronaphthoquinone. That is, no system or step for purifying a starting material and a product is necessitated so as to obtain a highly pure reaction product.

Another feature of the present process resides in that crude 5-nitronaphthoquinone in the form of a wet cake can be used as it is in reaction operation, so that the drying step for crude 5-nitronaphthoquinone can be omitted.

A further feature of the process is that even though an amount of solvent is reduced to a minimum of the defined range, the purity of product is hardly lowered, it being possible to increase a productivity of 5-nitrotetrahydroanthraquinone per unit volume of a reaction vessel.

In another embodiment (B) of the present invention, the production of highly pure 5-nitrotetrahydroanthraquinone from crude 5-nitronaphthoquinone is effected similarly to the process of the above embodiment (A) but the Diels-Alder condensation reaction of crude 5-nitronaphthoquinone with 1,3-butadiene is not necessarily required to be effected in the afore-defined solvent.

That is, the Diels-Alder condensation reaction may be effected in a convenient solvent such as an alcohol. The resultant crude 5-nitrotetrahydroanthraquinone which contains 6-nitrotetrahydroanthraquinone is dissolved under heating conditions in such a solvent as defined hereinbefore, i.e., benzene, an alkylated aromatic hydrocarbon, a halogenated aromatic hydrocarbon, a halogenated aliphatic hydrocarbon or a mixture thereof, followed by filtration and cooling the resulting filtrate to crystallize 5-nitrotetrahydroanthraquinone. The thus crystallized 5-nitrotetrahydroanthraquinone is separated by filtration to obtain 5-nitrotetrahydroanthraquinone with high purity. In this embodiment, highly pure 5-nitrotetrahydroanthraquinone is produced by using benzene, an alkylated aromatic hydrocarbon, a halogenated aromatic hydrocarbon or a halogenated aliphatic hydrocarbon as a solvent for the purification of crude 5-nitrotetrahydroanthraquinone which is obtained by reaction in a solvent other than the above-mentioned counterpart.

6-nitrotetrahydroanthraquinone-containing crude 5-nitrotetrahydroanthraquinone used in this process is a reaction product which is obtained, by Diels-Alder condensation reaction of crude 5-nitronaphthoquinone with 1,3-butadiene in an alcohol solvent in accordance with a known process, including the aforementioned process of Woroshtzov, and may contain up to 10 wt% of 6-nitrotetrahydroanthraquinone. Examples of the alcohol solvent are methanol, ethanol, n-propanol, iso-propanol, n-butanol, methoxyethanol and the like.

The amount of the solvent for purification is generally in the range of 1 to 10 times, preferably 1 to 5 times, by weight as much as that of crude 5-nitrotetrahydroanthraquinone employed. Though it is possible to use the solvent in an amount of 10 times or greater as much, the recovery percentage of 5-nitrotetrahydroanthraquinone will be unfavorably lowered.

The dissolution of crude 5-nitrotetrahydroanthraquinone in the solvent is effected under heating and agitating conditions. Though the heating temperature is not critical, it is generally within the range of 30° to either 100°C or a boiling point of the solvent employed under an atmospheric pressure, preferably 50° to 80°C. The solution is maintained with agitation at the above-defined temperature for 10 min to 2 hours, preferably 30 min to 1 hour, and then subjected to filtration to remove an insoluble matter therefrom. The resultant filtrate is cooled to separate 5-nitrotetrahydroanthraquinone as crystals. The cooling temperature is in the range of 5° to 30°C, preferably 10° to 20°C. The thus separated crystals are taken out by filtration, and, if desired, washed with a solvent such as methanol, ethanol, or isopropanol in an amount of 0.2 to 5 times by weight as much as that of the cake (on a dry weight basis) and dried at a temperature below 100°C under normal or reduced pressure to obtain highly pure 5-nitrotetrahydroanthraquinone.

When the thus obtained 5-nitrotetrahydroanthraquinone is oxidized into 1-nitroanthraquinone and reduced in accordance with the aforementioned standard method, there can be obtained 1-aminoanthraquinone with a purity of greater than 98 wt%. The 1-aminoanthraquinone has generally a 2-aminoanthraquinone content below 1 wt%, and the content may be reduced to below 0.5 wt% under suitable conditions. Impurities other than 2-aminoanthraquinone are scarcely detected. The recovery percentage of 5-nitrotetrahydroanthraquinone is generally above 90% and may be as high as 95% or greater, if 5-nitrotetrahydroanthraquinone is treated under suitable conditions.

By this process, crude 5-nitrotetrahydroanthraquinone which contains a relatively large amount of 6-nitrotetrahydroanthraquinone can be purified by a relatively simple apparatus and operation to obtain highly pure 5-nitrotetrahydroanthraquinone at high yield.

As will be understood from the foregoing, the process of the present invention, which is feasible in embodiment (A) or (B), is effective for producing highly pure 5-nitrotetrahydroanthraquinone from crude 5-nitronaphthoquinone which is used, as it is, without purification. The pure 5-nitrotetrohydroanthraquinone can be easily converted into highly pure 1-aminoanthraquinone. Thus, it will be understood that the process of the invention makes it possible to economically produce 1-aminoanthraquinone with high purity from starting crude 5-nitronaphthoquinone.

The present invention will be particularly illustrated by way of the following examples.

EXAMPLE 1

49.6 g of a crude 5-nitronaphthoquinone cake (which had a water content of 50 wt% and a dry weight of 24.8 g, and comprised of 82 wt% of 5-nitronaphthoquinone and 10 wt% of 6-nitronaphthoquinone when determined under dried condition by a gas chromatography), 12.1 g of 1,3-butadiene and 49.6 g of benzene were introduced into an autoclave, which was then hermetically sealed for reaction at 80°C for 2.5 hours. The resultant reaction solution was cooled to 25°–30°C to crystalize 5-nitrotetrahydroanthraquinone, subjected to filtration, washed with 40 g of methanol, and dried to obtain 22.4 g of 5-nitrotetrahydroanthraquinone. The yield was 87.0% of the theoretical (based on the 5-nitronaphthoquinone contained in the crude starting material).

The thus obtained 5-nitrotetrahydroanthraquinone was subjected to oxidation and reduction in accordance with the aforementioned standard method to obtain 1-aminoanthraquinone with a purity of greater than 98 wt%. The 1-aminoanthraquinone contained no diaminoanthraquinones but only 0.8 wt% of 2-aminoanthraquinone as impurity.

EXAMPLE 2

Example 1 was repeated except that 62 g of toluene was used instead of benzene and that the reaction was effected at 70°C for 4 hours to obtain 5-nitrotetrahydroanthraquinone at a yield of 88.0%. The thus obtained 5-nitrotetrahydroanthraquinone was oxidized and reduced by the standard method to obtain 1-aminoanthraquinone having a purity of 98 wt% or greater and a 2-aminoanthraquinone content as small as 0.5 wt%.

EXAMPLE 3

41.3 g of a crude 5-nitronaphthoquinone cake (having a water content of 40 wt% and a dry weight of 24.8 g, and comprised of 75 wt% of 5-nitronaphthoquinone and 15 wt% of 6-nitronaphthoquinone when determined under dried conditions), 13.1 g of 1,3-butadiene and 124 g of trichloroethylene were introduced into an autoclave. The autoclave was hermetically sealed and the reaction was effected at 80°C for 2.5 hours. Then, Example 1 was repeated to obtain 20.7 g of 5-nitrotetrahydroanthraquinone. The yield was 88.0%. The thus obtained 5-nitrotetrahydroanthraquinone was oxidized and reduced in accordance with the standard method to obtain 1-aminoanthraquinone having a purity above 98 wt% and a 2-aminoanthraquinone content of 0.5 wt%.

EXAMPLE 4

Example 3 was repeated using 248 g of perchloroethylene instead of trichloroethylene to obtain 5-nitrotetrahydroanthraquinone at a yield of 85.0%. Then, the product was subjected to oxidation and reduction in accordance with the standard method to obtain 1-aminoanthraquinone having a purity above 98 wt% and a 2-aminoanthraquinone content of 0.8 wt%.

When the above process was repeated using dry crude 5-nitronaphthoquinone cake instead of the wet cake, similar results were obtained.

EXAMPLE 5

Example 1 was repeated using 74.4 g of o-dichlorobenzene instead of benzene to obtain 5-nitrotetrahydroanthraquinone at a yield of 87.0%. This product was subjected to oxidation and reduction in accordance with the standard method to obtain 1-aminoanthraquinone having a purity above 98 wt% and a 2-aminoanthraquinone content of 0.5 wt%.

EXAMPLE 6

Example 3 was repeated using 124 g of tetrachloroethane instead of trichloroethylene to obtain 5-nitrotetrahydroanthraquinone at a yield of 85.5%. The thus obtained 5-nitrotetrahydroanthraquinone was subjected to oxidation and reduction in accordance with the standard method to obtain 1-aminoanthraquinone having a purity above 98 wt% and a 2-aminoanthraquinone content of 0.5 wt%.

EXAMPLE 7

Example 3 was repeated using 74.4 g of chloronaphthalene instead of trichloroethylene to obtain 5-nitrotetrahydroanthraquinone at a yield of 87.0%, which was then subjected to oxidation and reduction in accordance with the standard method to obtain 1-aminoanthraquinone having a purity above 98 wt% and a 2-aminoanthraquinone content of 0.8 wt%.

EXAMPLE 8

30 g of crude 5-nitrotetrahydroanthraquinone comprised of 93 wt% of 5-nitrotetrahydroanthraquinone and 7 wt% of 6-nitrotetrahydroanthraquinone was introduced into 150 g of toluene for dissolution at about 80°C for 1 hour with agitation, followed by filtration. The filtrate was cooled to 10°–15°C to crystallize 5-nitrotetrahydroanthraquinone. The crystals were separated by filtration and the resultant cake was washed with 10 g of ethanol and dried to obtain 24.9 g of 5-nitrotetrahydroanthraquinone. The recovery percentage was 89.2% (based on the 5-nitrotetrahydroanthraquinone contained in the crude starting material). The thus obtained product was subjected to oxidation and reduction in accordance with the standard method to obtain 1-aminoanthraquinone having a purity above 98 wt% and a 2-aminoanthraquinone content below 0.5 wt%.

EXAMPLE 9

30 g of crude 5-nitrotetrahydroanthraquinone having the same composition as in Example 8 was introduced into 450 g of trichloroethylene and dissolved at about 80°C for 1 hour while agitation, followed by filtration. The resultant filtrate was treated in the same manner as in Example 8 to obtain 25.4 g of 5-nitrotetrahydroanthraquinone. The recovery percentage was 91.0% (based on 5-nitrotetrahydroanthraquinone contained in the starting material). The thus obtained 5-nitrotetrahydroanthraquinone was subjected to oxidation and reduction in accordance with the standard method to obtain 1-aminoanthraquinone having a purity above 98 wt% and a 2-aminoanthraquinone content of 0.5 wt%.

EXAMPLE 10

Example 1 was repeated except that 49.6 g of xylene was used instead of 49.6 g of benzene and the reaction was effected at 80°C for 2 hours. The resulting reaction solution was cooled to 25°–30°C to crystalize 5-nitrotetrahydroanthraquinone, subjected to filtration, washed with 40 g of methanol and then about 100 ml of water, and dried to obtain 22.9 g of 5-nitrotetrahydroanthraquinone. The yield was 89.0%. The thus obtained 5-nitrotetrahydroanthraquinone was subjected to oxidation and reduction in accordance with the standard method to obtain 1-aminoanthraquinone having a purity above 98.0 wt% and a 2-aminoanthraquinone content of 0.5 wt%.

COMPARATIVE EXAMPLE 1

24.8 g of crude 5-nitronaphthoquinone (comprised of 82 wt% of 5-nitronaphthoquinone and 10 wt% of 6-nitronaphthoquinone), 12.1 g of 1,3-butadiene, and 124 g of ethanol were introduced into an autoclave. The autoclave was hermetically sealed and the reaction was effected at about 80°C for 2.5 hours. The resultant reaction solution was cooled to 25°–30°C to crystalize 5-nitrotetrahydroanthraquinone, and filtered. The cake was washed with 40 g of ethanol and dried to obtain 22.9 g of 5-nitrotetrahydroanthraquinone. The yield was 89.0%.

The thus obtained 5-nitrotetrahydroanthraquinone was subjected to oxidation and reduction in accordance with the standard method to obtain 1-aminoanthraquinone having a purity of about 96 wt% and a 2-aminoanthraquinone content as great as 3 – 5 wt%.

COMPARATIVE EXAMPLE 2

Comparative Example 1 was repeated using 49.6 g of nitrobenzene instead of 124 g of ethanol to obtain 18.5 g of 5-nitrotetrahydroanthraquinone. The yield was 72.0%. The thus obtained 5-nitrotetrahydroanthraquinone was subjected to oxidation and reduction in accordance with the standard method to obtain 1-aminoanthraquinone having a purity above 98 wt% and a 2-aminoanthraquinone content of 0.9%.

COMPARATIVE EXAMPLE 3

Comparative Example 1 was repeated using 248 g of methoxyethanol instead of 124 g of ethanol to obtain 20.0 g of 5-nitrotetrahydroanthraquinone. The yield from 5-nitronaphthoquinone was 78%.

The thus obtained 5-nitrotetrahydroanthraquinone was subjected to oxidation and reduction in accordance with the standard method to obtain 1-aminoanthraquinone having a purity of about 95 wt% and a 2-aminoanthraquinone content as high as 4 – 5 wt%.

What is claimed is:

1. In a process for preparing 5-nitro-1,4,4a,9a-tetrahydroanthraquinone by the reaction of 5-nitro-1,4-naphthoquinone with 1,3-butadiene in a solvent, the improvement comprising cooling either a solution which is obtained by reacting 5-nitro-1,4-naphthoquinone with 1,3-butadiene in a solvent selected from the group consisting of benzene, an alkylated aromatic hydrocarbon, a halogenated aromatic hydrocarbon, a halogenated aliphatic hydrocarbon and a mixture thereof or a solution which is obtained by reacting 5-nitro-1,4-naphthoquinone with 1,3-butadiene and dissolving the resulting product under heating conditions in the above-defined solvent to crystallize 5-nitro-1,4,4a,9a-tetrahydroanthraquinone, and separating the crystallized 5-nitro-1,4,4a,9a-tetrahydroanthraquinone by filtration.

2. A process according to claim 1, comprising the steps of reacting 5-nitro-1,4-naphthoquinone with 1,3-butadiene in said solvent, cooling the reaction solution to crystallize 5-nitro-1,4,4a,9a-tetrahydroanthraquinone, and separating the crystallized 5-nitro-1,4,4a,9a-tetrahydroanthraquinone by filtration.

3. A process according to claim 1, comprising the steps of dissolving in said solvent under heating conditions 5-nitro-1,4,4a-9a-tetrahydroanthraquinone which is obtained by reaction of 5-nitro-1,4-naphthoquinone with 1,3-butadiene, subjecting the solution to filtration, cooling the filtrate to crystallize 5-nitro-1,4,4a,9a-tetrahydroanthraquinone, and separating said 5-nitro-1,4,4a,9a-tetrahydroanthraquinone by filtration.

4. A process according to claim 1, wherein said solvent is an alkylated aromatic hydrocarbon having one to three substituted alkyl groups containing 1 to 4 carbon atoms.

5. A process according to claim 1, wherein said solvent is a halogenated aromatic hydrocarbon which has one to three halogen atoms.

6. A process according to claim 1, wherein said solvent is a halogenated aliphatic hydrocarbon having one to four substituted halogen atoms and 1 to 4 carbon atoms.

7. A process according to claim 1, wherein said solvent is benzene.

8. A process according to claim 1, wherein said solvent is selected from the group consisting of toluene and xylene.

9. A process according to claim 1, wherein said solvent is selected from the group consisting of monochlorobenzene and dichlorobenzene.

10. A process according to claim 1, wherein said solvent is selected from the group consisting of trichloroethylene and perchloroethylene.

11. A process according to claim 2, wherein said 5-nitro-1,4-naphthoquinone is crude 5-nitro-1,4-naphthoquinone which contains in a dry state up to 20 wt% of 6-nitro-1,4-naphthoquinone.

12. A process according to clam 2, wherein said 5-nitro-1,4-naphthoquinone is crude 5-nitro-1,4-naphthoquinone in the form of wet cake which contains up to 50 wt% of water.

13. A process according to claim 3, wherein said 5-nitro-1,4,4a,9a-tetrahydroanthraquinone which is obtained by reacting 5-nitro-1,4-naphthoquinone with 1,3-butadiene contains up to 10 wt% of an isomer, 6-nitro-1,4,4a,9a-tetrahydroanthraquinone.

* * * * *